United States Patent
Tamura et al.

(10) Patent No.: US 10,894,762 B2
(45) Date of Patent: *Jan. 19, 2021

(54) PROCESS FOR PRODUCING UNSATURATED NITRILE

(71) Applicant: ASAHI KASEI KABUSHIKI KAISHA, Tokyo (JP)

(72) Inventors: Sho Tamura, Tokyo (JP); Dai Nagata, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 15 days.

This patent is subject to a terminal disclaimer.

(21) Appl. No.: 16/307,664

(22) PCT Filed: May 21, 2018

(86) PCT No.: PCT/JP2018/019460
§ 371 (c)(1),
(2) Date: Dec. 6, 2018

(87) PCT Pub. No.: WO2019/008924
PCT Pub. Date: Jan. 10, 2019

(65) Prior Publication Data
US 2020/0087251 A1    Mar. 19, 2020

(30) Foreign Application Priority Data

Jul. 3, 2017  (JP) ................. 2017-130390

(51) Int. Cl.
  *C07C 253/26*  (2006.01)
  *B01J 8/18*  (2006.01)
  *C07B 43/08*  (2006.01)

(52) U.S. Cl.
  CPC .......... *C07C 253/26* (2013.01); *B01J 8/1827* (2013.01); *C07B 43/08* (2013.01); *B01J 2208/00938* (2013.01)

(58) Field of Classification Search
  CPC .................................................. C07C 253/26
  See application file for complete search history.

(56) References Cited

U.S. PATENT DOCUMENTS 4,246,191 A   1/1981  Pujado
4,801,731 A   1/1989  Jordan

FOREIGN PATENT DOCUMENTS

| JP | 2-000258 A | 1/1990 |
| JP | 10-152463 A | 6/1998 |
| JP | 2002-193906 A | 7/2002 |
| JP | 2007-063089 A | 3/2007 |
| JP | 2016-210740 A | 12/2016 |
| WO | WO 2016/147950 A1 | 9/2016 |

OTHER PUBLICATIONS

English translation of International Preliminary Report on Patentability and Written Opinion dated Jan. 16, 2020, in PCT/JP2018/019460 (Forms PCT/IB/326, PCT/IB/373, and PCT/ISA/237).
Extended European Search Report, dated Jul. 9, 2020, for European Application No. 18825853.7.

*Primary Examiner* — Shawquia Jackson
(74) *Attorney, Agent, or Firm* — Birch, Stewart, Kolasch & Birch, LLP

(57) ABSTRACT

A process for producing unsaturated nitrile, using a fluidized bed reactor and comprising a reaction step of subjecting hydrocarbon to a vapor phase catalytic ammoxidation reaction in the presence of a catalyst to produce the corresponding unsaturated nitrile, wherein when an internal space of the reactor is divided into two spaces of an upper space occupying a space from an upper end of an inlet of a cyclone to an upper end of the internal space and a lower space occupying a space below the upper end of the inlet of the cyclone and ranging to a dispersion plate, a ratio of an existing amount of the catalyst in the upper space to an existing amount of the catalyst in the lower space is 0.05 to 0.45 in the reaction step.

6 Claims, 2 Drawing Sheets

PROCESS FOR PRODUCING UNSATURATED NITRILE

TECHNICAL FIELD

The present invention relates to a process for producing unsaturated nitrile.

BACKGROUND ART

Conventionally, a fluidized bed reactor has been widely used when alkane and/or alkene is subjected to a vapor phase catalytic ammoxidation reaction in the presence of a metal composite oxide catalyst. In a fluidized bed reactor used on an industrial scale, the production operation is continuously carried out for a long period of time, and therefore, a decrease in catalytic activity exerting influence on the reaction yield, reduction of the amount of a catalyst charged due to outflow of the catalyst, and a change in particle size distribution of a catalyst or the like are brought about. On that account, for the purpose of improving a reaction yield of unsaturated nitrile, development of catalysts, improvement in internal equipment of the reactor, etc. have been made.

For example, for the purpose of providing a process for stably producing α,β-unsaturated nitrile such as acrylonitrile in a high yield over a long period of time by suppressing deterioration of a metal oxide catalyst, Patent Literature 1 discloses a vapor phase catalytic oxidation reaction method for hydrocarbon, wherein when alkane having 2 to 8 carbon atoms and/or alkene having 2 to 8 carbon atoms is subjected to a reaction of vapor phase catalytic oxidation using a fluidized bed reactor in the presence of ammonia and a metal composite oxide catalyst, the temperature of a zone where the flow density of the catalyst in the fluidized bed reactor is 50 kg/m$^3$ or less is set to be lower than the temperature of a zone where the catalyst flow density is 300 kg/m$^3$ or more.

CITATION LIST

Patent Literature

Patent Literature 1: Japanese Patent Laid-Open No. 2002-193906

SUMMARY OF INVENTION

Technical Problems

In the case where the interior of a fluidized bed reactor is divided into a dense catalyst zone and a sparse catalyst zone for convenience when a reaction step is carried out, the dense catalyst zone is a zone mainly purposing a reaction, and therefore, various studies have been made on the dense catalyst zone in order that the starting material gas concentration, oxygen concentration, feeding manner, temperature, etc. should not cause deterioration of the catalyst. Patent Literature 1 focuses on the temperature of the sparse catalyst zone rather than the dense catalyst zone, and is intended to stably produce α,β-unsaturated nitrile such as acrylonitrile in a high yield over a long period of time by suppressing deterioration of a metal oxide catalyst, but the decrease in the yield of unsaturated nitrile is not only attributable to the deterioration of catalyst. According to the studies by the present inventors, it has been found that a part of unsaturated nitrile produced in a lower space (dense catalyst zone) of the fluidized bed reactor further reacts with a catalyst in an upper space (sparse catalyst zone) and is decomposed.

The present invention has been made in the light of the above problem, and it is an object of the present invention to provide a process for producing unsaturated nitrile in which the unsaturated nitrile can be obtained in a high yield by suppressing decomposition of unsaturated nitrile produced in the fluidized bed reactor.

Solutions to Problems

That is, the present invention is as follows.

A process for producing unsaturated nitrile, using a fluidized bed reactor comprising an internal space comprising a catalyst capable of being fluidized therein; a starting material feed opening to feed a starting material gas comprising hydrocarbon to the internal space; a dispersion plate to feed an oxygen-containing gas comprising oxygen to the internal space; a discharge port to discharge a reaction product gas from the internal space; and a cyclone to separate and recover the catalyst from the reaction product gas in the internal space, the process comprising a reaction step of subjecting the hydrocarbon to a vapor phase catalytic ammoxidation reaction in the presence of the catalyst in the internal space to produce the corresponding unsaturated nitrile, wherein when the internal space is divided into two spaces of an upper space occupying a space from an upper end of an inlet of the cyclone to an upper end of the internal space and a lower space occupying a space below the upper end of the inlet of the cyclone and ranging to the dispersion plate, a ratio of an existing amount of the catalyst in the upper space per unit volume to an existing amount of the catalyst in the lower space per unit volume is 0.05 to 0.45 in the reaction step.

The process for producing the unsaturated nitrile according to [1], wherein the existing amount of the catalyst in the upper space per unit volume is 10 kg/m$^3$ or more and 100 kg/m$^3$ or less in the reaction step.

The process for producing the unsaturated nitrile according to [1] or [2], wherein the existing amount of the catalyst in the lower space per unit volume is 150 kg/m$^3$ or more and 600 kg/m$^3$ or less in the reaction step.

The process for producing the unsaturated nitrile according to any one of [1] to [3], wherein a superficial gas velocity in the upper space is less than 1.0 m/s in the reaction step.

The process for producing the unsaturated nitrile according to any one of [1] to [4], wherein an oxygen concentration in the reaction product gas discharged from the discharge port is 0.5 to 5.0 vol % in the reaction step.

The process for producing the unsaturated nitrile according to any one of [1] to [5], wherein the hydrocarbon is propane and/or propylene.

Advantageous Effects of Invention

According to the present invention, a process for producing unsaturated nitrile in which the unsaturated nitrile can be obtained in a high yield by suppressing decomposition of the unsaturated nitrile produced in the fluidized bed reactor can be provided.

DESCRIPTION OF EMBODIMENTS

Figure 1:
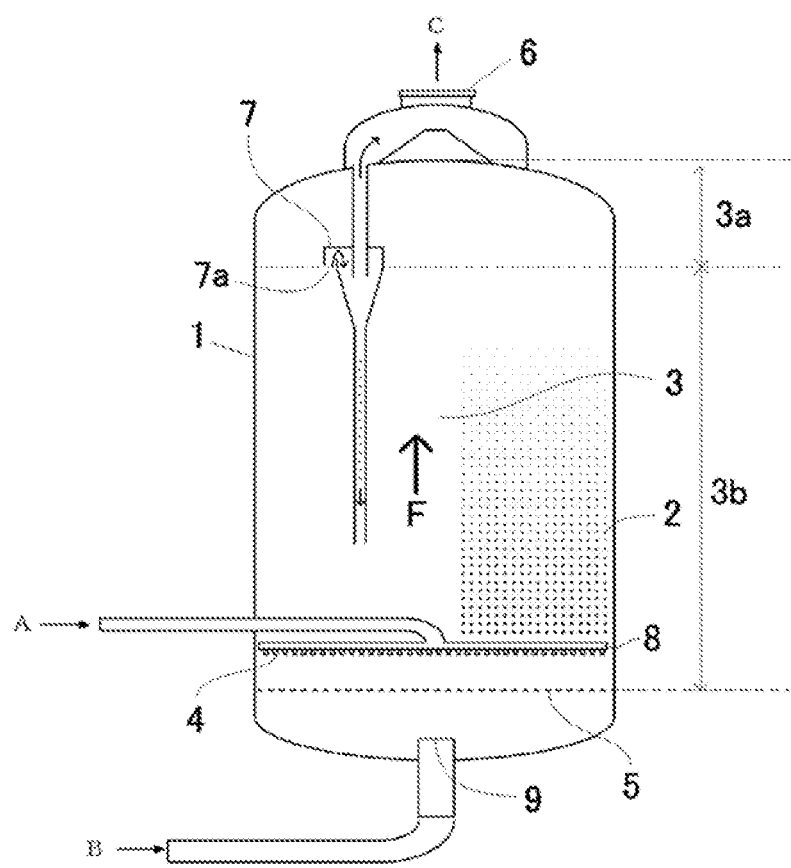
FIG. 1 shows a schematic sectional view of a fluidized bed reactor that can be used in the process for producing unsaturated nitrile of the present embodiment.

An embodiment of the present invention (referred to as the "present embodiment" hereinafter) is described below in detail, but the present invention is not limited to this and can be variously modified without departing from the spirit of the present invention. In the drawings, the same elements are denoted by the same reference characters, and a repeated description thereof may be omitted. Unless otherwise noted, the positional relations such as up and down and left and right are based on the positional relations shown in the drawings. Further, the dimension ratios in the drawings are not limited to the ratios illustrated.

[Process for Producing Unsaturated Nitrile]

The process for producing unsaturated nitrile of the present embodiment is a process using a fluidized bed reactor comprising an internal space comprising a catalyst capable of being fluidized therein; a starting material feed opening to feed a starting material gas comprising hydrocarbon to the internal space; a dispersion plate to feed an oxygen-containing gas comprising oxygen to the internal space; a discharge port to discharge a reaction product gas from the internal space; and a cyclone to separate and recover the catalyst from the reaction product gas in the internal space, the process comprising a reaction step of subjecting the hydrocarbon to a vapor phase catalytic ammoxidation reaction in the presence of the catalyst in the internal space to produce the corresponding unsaturated nitrile, wherein when the internal space is divided into two spaces of an upper space occupying a space from an upper end of an inlet of the cyclone to an upper end of the internal space and a lower space occupying a space below the upper end of the inlet of the cyclone and ranging to the dispersion plate, a ratio of an existing amount of the catalyst in the upper space per unit volume to an existing amount of the catalyst in the lower space per unit volume is 0.05 to 0.45 in the reaction step. In the case where a plurality of measurement results is present depending upon the measurement locations, the existing amount of the catalyst in the upper space per unit volume is the lowest value of the measured values, and the existing amount of the catalyst in the lower space per unit volume is the highest value of the measured values.

In FIG. 1, a schematic sectional view of a fluidized bed reactor that can be used in the process for producing unsaturated nitrile of the present embodiment is shown. A fluidized bed reactor 1 to carry out a vapor phase catalytic ammoxidation reaction is installed in such a way that the direction of an arrow F becomes a substantially vertical direction to the ground surface, and the fluidized bed reactor 1 comprises an internal space 3 containing a catalyst 2 capable of being fluidized therein; a starting material feed opening 4 to feed a starting material gas A containing hydrocarbon to the internal space 3; a dispersion plate 5 to feed an oxygen-containing gas B containing oxygen to the internal space; a discharge port 6 to discharge a reaction product gas C from the internal space 3; and a cyclone 7 to separate and recover the catalyst 2 from the reaction product gas in the internal space 3. The starting material gas A containing hydrocarbon is fed to the internal space 3 from the starting material feed opening 4 through a dispersion tube 8. The fluidized bed reactor 1 may have a feed opening 9 to feed the oxygen-containing gas B. The oxygen-containing gas B introduced into the internal space 3 from the feed opening 9 is dispersed by the dispersion plate 5. The starting material gas A to be fed from a plurality of the starting material feed openings 4 and the oxygen-containing gas B to be fed by being dispersed by the dispersion plate 5 are fed in such a way that these gases face each other, and they are blended while being intermingled with each other.

The catalyst 2 is fluidized in the internal space 3 with a balance among the weight and the volume of the catalyst itself, the feed rates of the starting material gas A and the oxygen-containing gas B (flow rates in the direction of the arrow F), etc. In the zone above the dispersion tube 8, the existing amount (distribution) of the catalyst 2 in the internal space 3 per unit space decreases toward the upper part from the lower part of the internal space 3 (in the direction of the arrow F).

The average particle diameter of the catalyst 2 is preferably 35 to 75 μm. The bulk density of the catalyst 2 is preferably 0.85 to 1.2 g/cc.

The internal space 3 may have, in addition to the cyclone 7 to separate and recover the catalyst 2 from the reaction product gas, a cooling coil (not shown) to mainly remove heat of reaction of the lower space of the internal space 3 and thereby control the reaction temperature and a member (not shown) to control the superficial gas velocity in the internal space 3, when needed. The superficial gas velocity in the internal space 3 varies with a cross-sectional area of the internal space 3 (area in a direction orthogonally intersecting with the direction of the arrow F). For example, when an internal space 3 whose cross-sectional areas are not uniform is supposed, the superficial gas velocity decreases at a place having a large cross-sectional area, and the superficial gas velocity increases at a place having a small cross-sectional area. From the viewpoint of control of the superficial gas velocity at each place of the internal space 3, the member to control the superficial gas velocity is installed in the internal space 3, and the gas-flowable cross-sectional area at a place where the member to control the superficial gas velocity is installed is narrowed by a portion occupied by the member to control the superficial gas velocity, so that the superficial gas velocity at this place increases as compared with that at a place where the member to control the superficial gas velocity is not installed. Instead of installing the member to control the superficial gas velocity, a fluidized bed reactor 1 whose diameters are not uniform so that the cross-sectional area of the internal space 3 may vary at the desired place may be used.

The reaction product gas accompanied by the catalyst 2 enters the cyclone 7 through an inlet 7a. The catalyst 2 having entered the cyclone 7 falls downward in the internal space 3 so as to be spiral in the conical section of the cyclone 7, while the reaction product gas is guided to the discharge port 6 by a tube extending upward from the upper part of the cyclone 7. Below the conical section of the cyclone 7, a tube further extends downward in the internal space 3, and through this tube, the catalyst 2 is guided downward in the internal space 3.

[Reaction Step]

The reaction step is a step of subjecting hydrocarbon to a vapor phase catalytic ammoxidation reaction in the presence of a catalyst to produce the corresponding unsaturated nitrile. The vapor phase catalytic ammoxidation reaction takes place mainly in the lower space 3b.

The hydrocarbon is not specifically restricted, and examples thereof include alkanes, such as methane, ethane, propane, n-butane and isobutane; and alkenes, such as ethylene, propylene, n-butylene and isobutylene. Of these, propane, isobutane, propylene and isobutylene are preferable, and propane and/or propylene is more preferable, from the viewpoint of values of the resulting nitrile compound as an intermediate material for chemicals.

In the starting material gas A, starting materials other than hydrocarbon may be contained. Examples thereof include ammonia, oxygen and air. As previously described, oxygen, air or the like can also be fed as the oxygen-containing gas B separately from the starting material gas A.

The catalyst is not specifically restricted as long as it is a solid catalyst usually used for the reaction, and for example, a metal oxide catalyst supported on silica or the like can be used.

The composition of the catalyst is not specifically restricted as long as it has an activity against the vapor phase catalytic ammoxidation reaction, but from the viewpoint that the action and effect of the present invention are exerted more effectively and more surely, an oxide catalyst containing at least molybdenum as an element is preferable. More specifically, a catalyst having a composition represented by the following formula (1) can be used.

$$MoV_aNb_bX_cT_dZ_eO_n \quad (1)$$

wherein, a, b, c, d, e and n each represents an atomic ratio of each atom per Mo atom, and are in the ranges of $0.01 \leq a \leq 1$, $0.01 \leq b \leq 1$, $0.01 \leq c \leq 1$, $0 \leq d \leq 1$, and $0 \leq e < 1$, and n is a value satisfying a balance of the valences.

Per Mo atom, the atomic ratio a of V is preferably 0.1 or more and 0.4 or less, and the atomic ratio b of Nb is preferably 0.01 or more and 0.2 or less. The atomic ratio c of the X component per Mo atom is preferably 0.01 or more and 0.6 or less, and is more preferably 0.1 or more and 0.4 or less.

The element represented by X is one or more elements selected from the group consisting of, for example, Sb, Te, Sr, Cr, Ta, Rh, Pd, Pt and Ag. Examples of compounds containing these elements include nitrates, carboxylates, carboxylic acid ammonium salts, peroxocarboxylates, peroxocarboxylic acid ammonium salts, halogenated ammonium salts, halides, acetylacetonates and alkoxides. Of these, aqueous starting materials represented by nitrates and carboxylates are preferably used.

As the elements represented by X, Te and Sb are preferable. In the industrial production process for unsaturated nitrile, properties of withstanding long-term use at not lower than 400° C. are generally required, and it is particularly preferable to use Sb as the element represented by X. On the other hand, in the industrial production process for an unsaturated acid, a reaction at not higher than 400° C. is also possible, and therefore, influence by escaping of Te in the long-term operation is small, so that also Te can be preferably used.

d that is an atomic ratio of an element represented by T per Mo atom is preferably 0 or more and less than 1, more preferably 0.001 or more and less than 0.1, and still more preferably 0.002 or more and less than 0.08. The element represented by T is preferably one or more elements selected from the group consisting of Ti, Zr, Hf, W, Mn, Re, Fe, Co, Ni, Au, Zn, B, Al, Ga, In, Ge, Sn and Bi, and is more preferably Ti, W or Mn.

e that is an atomic ratio of an element represented by Z per Mo atom is preferably 0 or more and less than 1, and more preferably 0.0001 or more and less than 0.5. As the elements represented by Z, preferable are alkaline earth elements and rare earth elements, more preferable are Ba, Sc, Y, La, Ce, Pr and Yb, and particularly preferable is Ce. From the viewpoint of enhancement in yield of unsaturated nitrile in the ammoxidation reaction, it is preferable that the oxide catalyst contain an element represented by Z, and it is more preferable that the elements be homogeneously dispersed in a catalyst particle.

Examples of compounds containing Mo, which become starting materials for Mo in the catalyst, (referred to as "Mo-containing compounds" hereinafter, the same shall apply to other elements) include ammonium molybdate oxide, ammonium heptamolybdate, phosphomolybdic acid and silicomolybdic acid, and of these, ammonium heptamolybdate [$(NH_4)_6Mo_7O_{24} \cdot 4H_2O$] can be preferably used.

Examples of V-containing compounds that become starting materials for V in the catalyst include vanadium pentoxide, ammonium metavanadate and vanadyl sulfate, and of these, ammonium metavanadate [$NH_4VO_3$] can be preferably used.

Examples of Nb-containing compounds that become starting materials for Nb in the catalyst include niobic acid, inorganic acid salts of niobium and organic acid salts of niobium, and of these, niobic acid can be preferably used.

When Te is used as an element represented by X, telluric acid [$H_6TeO_6$] can be preferably used as a starting material for Te in the catalyst, and when Sb is used, antimony oxide, particularly antimony trioxide [$Sb_2O_3$], can be preferably used as a starting material for Sb in the catalyst.

When the oxide catalyst is supported on silica, silica sol, powder silica or the like can be added as a starting material for silica. The powder silica is preferably one produced by a pyrogenic method, and by dispersing the powder silica in water in advance and using the resulting dispersion, addition to a slurry and mixing become easy. The dispersing method is not specifically restricted, and dispersing can be carried out using general homogenizer, homomixer, ultrasonic vibrator, etc. singly or in combination.

The oxide catalyst can be obtained by preparing an aqueous solution or an aqueous dispersion of these starting materials and subjecting the solution or the dispersion to drying and calcining in accordance with conventional methods.

Figure 2:
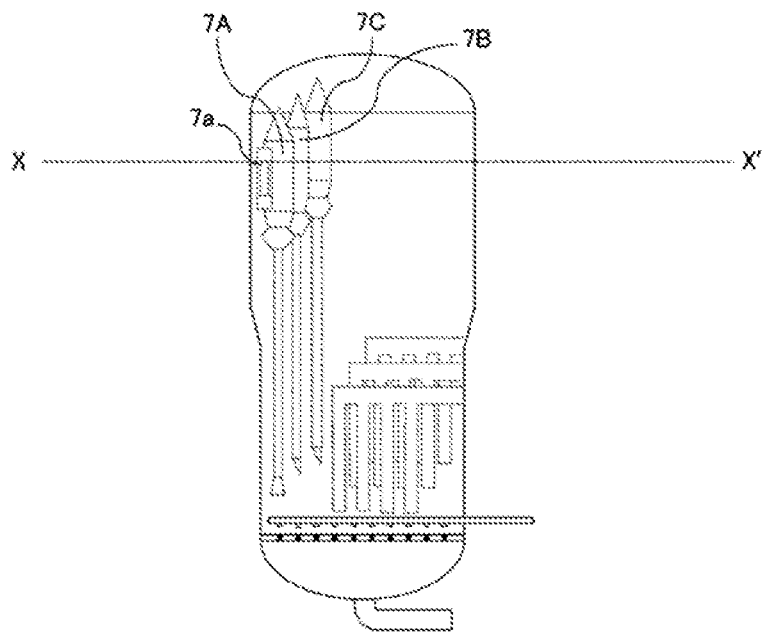
FIG. 2 shows a schematic sectional view to describe an upper end of an inlet of the cyclone of the present embodiment.

In the present embodiment, the internal space 3 is defined by dividing it into two spaces of an upper space 3a occupying a space from an upper end of an inlet 7a of the cyclone 7 to an upper end of the internal space 3 and a lower space 3b occupying a space below the inlet 7a of the cyclone and ranging to the dispersion plate 5. The "upper end of an inlet of the cyclone" refers to the uppermost end of an opening of the cyclone inlet, and when a plurality of cyclones are present in a single stage, it refers to the uppermost end of an opening that is at the highest position. When a plurality of cyclones are present in multiple stages, an opening of a cyclone in the first stage is only taken into consideration, but openings of cyclones in the second and subsequent stages are not taken into consideration. For example, as shown in FIG. 2, in the case of multi-stage cyclones 7A to 7C, the upper end of an inlet of a cyclone, which is indicated by a line segment X-X', means the uppermost end of the opening of the cyclone 7A in the first stage.

At this time, the ratio of an existing amount of the catalyst in the upper space 3a per unit volume to an existing amount of the catalyst in the lower space 3b per unit volume is 0.05 to 0.45, preferably 0.05 to 0.40, and more preferably 0.06 to 0.35. By specifying the ratio of the existing amount of the catalyst in the upper space 3a per unit volume to the existing amount of the catalyst in the lower space 3b per unit volume to 0.05 or more, fluidity in the lower space 3b is ensured, and the reaction efficiency of the vapor phase catalytic ammoxidation reaction is further enhanced. By specifying the ratio of the existing amount of the catalyst in the upper space 3a per unit volume to the existing amount of the catalyst in the lower space 3b per unit volume to 0.45 or less, the unsaturated nitrile produced in the lower space 3b can be inhibited from being decomposed in the upper space 3a, and the yield of the resulting unsaturated nitrile is further enhanced.

In the reaction step, the existing amount of the catalyst 2 in the upper space 3a per unit volume is preferably 10 kg/m$^3$ or more and 100 kg/m$^3$ or less, more preferably 15 kg/m$^3$ or more and 90 kg/m$^3$ or less, and still more preferably 15 kg/m$^3$ or more and 80 kg/m$^3$ or less. By specifying the existing amount of the catalyst 2 in the upper space 3a per unit volume to 10 kg/m$^3$ or more, fluidity in the lower space 3b is ensured, and the reaction efficiency of the vapor phase catalytic ammoxidation reaction tends to be further enhanced. By specifying the existing amount of the catalyst 2 in the upper space 3a per unit volume to less than 100 kg/m$^3$, the unsaturated nitrile produced in the lower space 3b can be inhibited from being decomposed in the upper space 3a, and the yield of the resulting unsaturated nitrile tends to be further enhanced.

In the reaction step, the existing amount of the catalyst 2 in the lower space 3b per unit volume is preferably 150 kg/m$^3$ or more and 600 kg/m$^3$ or less, more preferably 250 kg/m$^3$ or more and 550 kg/m$^3$ or less, and still more preferably 300 kg/m$^3$ or more and 500 kg/m$^3$ less than. By specifying the existing amount of the catalyst 2 in the lower space 3b per unit volume to 150 kg/m$^3$ or more, the yield in the vapor phase catalytic ammoxidation reaction tends to be further enhanced. By specifying the existing amount of the catalyst 2 in the lower space 3b per unit volume to less than 600 kg/m$^3$, fluidity in the lower space 3b tends to be further enhanced.

As a technique to control the existing amount of the catalyst in the upper space per unit volume, the existing amount of the catalyst in the lower space per unit volume, and the ratio of the existing amount of the catalyst to the above ranges, a technique of controlling the superficial gas velocity at each place in the reactor, a technique of controlling the bulk specific gravity of the catalyst, or a technique of a combination of them can be used.

The "existing amount of the catalyst per unit volume" in the present embodiment can be calculated from the following formula using a fluidized bed differential pressure. In the internal space of the fluidized bed reactor, the pressure at each height is measured by a manometer installed at each of a plurality of measurement points different in height, and the existing amount of the catalyst is calculated, whereby the existing amount of the catalyst in each of the upper space and the lower space can be specified.

Existing amount of catalyst of height from h1 to h2 (>h1) per unit volume=(differential pressure between h2-h1)/(distance between h2-h1)

In the case where a plurality of measurement results are present depending upon the measurement locations, the existing amount of the catalyst in the upper space per unit volume is the lowest value of the measured values, and the existing amount of the catalyst in the lower space per unit volume is the highest value of the measured values.

In the reaction step, the superficial gas velocity in the upper space 3a is preferably less than 1.0 m/sec, more preferably less than 0.95 m/sec, and still more preferably less than 0.9 m/sec. Since the superficial gas velocity is less than 1.0 m/sec, the existing amount of the catalyst in the upper space can be reduced, and the unsaturated nitrile produced in the lower space 3b can be inhibited from being decomposed in the upper space 3a, so that the yield of the resulting unsaturated nitrile tends to be further enhanced. The lower limit of the superficial gas velocity in the upper space 3a is not specifically restricted, but the superficial gas velocity is preferably 0.1 m/sec or more, more preferably 0.3 m/sec or more, and still more preferably 0.4 m/sec or more. The superficial gas velocity in the present embodiment can be calculated from the following formula. In the following formula, the "maximum cross-sectional area" is a cross-sectional area of the largest section of sections of the reactor body cut in a direction horizontal to the ground surface. The "gas flow rate" is determined by the total amount of gases fed to the internal space, such as starting material gas and oxygen-containing gas.

Superficial gas velocity (m/sec)=gas flow rate (m$^3$/hr)/maximum cross-sectional area (m$^2$)/3600

In the reaction step, the oxygen concentration in the reaction product gas C discharged from the discharge port 6 is preferably 0.5 vol % or more, more preferably 0.7 vol % or more, and still more preferably 1.0 vol % or more. The oxygen concentration in the reaction product gas C discharged from the discharge port 6 is preferably 5.0 vol % or less, more preferably 4.5 vol % or less, and still more preferably 4.0 vol % or less. Since the oxygen concentration in the reaction product gas C is 0.5 vol % or less, the catalyst can be inhibited from being excessively reduced. Since the oxygen concentration in the reaction product gas C is 5.0 vol % or less, the unsaturated nitrile produced in the lower space 3b can be inhibited from being decomposed in the upper space 3a, and the yield of the resulting unsaturated nitrile tends to be enhanced. The oxygen concentration in the reaction product gas C can be controlled by the feed rate of the oxygen-containing gas B or the reaction conditions.

EXAMPLES

The present invention will be more specifically described below with reference to examples and comparative examples. The present invention is in no way limited to the following examples.

Example 1

A fluidized bed reactor similar to that shown in FIG. 1 was prepared. The fluidized bed reactor was in the form of a vertical cylinder having an inner diameter of 0.6 m and a length of 17.5 m, had a dispersion plate 5 at the position of 1 m from a lower end of an internal space 3 and a starting material feed opening 4 above the dispersion plate in such a way that they faced each other, and had the uppermost end of an opening of a cyclone 7 at the position of 15.5 m from an upper end of the internal space 3. Manometers to measure pressures in the internal space were installed at the upper end of the dispersion plate 5, at the upper end of an inlet 7a of the cyclone 7 and at the upper end of the internal space 3.

The fluidized bed reactor was filled with 550 kg of a catalyst $(Mo_1V_{0.207}Sb_{0.219}Nb_{0.102}W_{0.030}Ce_{0.005}O_n/51.0$ wt %-$SiO_2)$ described in Example 1 of Japanese Patent No. 5694379, and propane and ammonia that were reaction starting materials were fed from the starting material feed opening 4 and air was fed from the dispersion plate 5 through a feed opening 9 in such a way that the propane:ammonia:oxygen molar ratio became 1:1.1:2.8 at a reaction temperature of 445° C. and a reaction pressure of 0.60 K/G. The yield of acrylonitrile after 3 hours (immediately after starting) and the yield of acrylonitrile after one week, from the initiation of the vapor phase catalytic ammoxidation reaction, are set forth in Table 1.

Example 2

A vapor phase catalytic ammoxidation reaction was carried out in the same manner as in Example 1, except that the catalytic amount was changed to 600 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 3

A vapor phase catalytic ammoxidation reaction was carried out in the same manner as in Example 1, except that the catalytic amount was changed to 500 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 4

A vapor phase catalytic ammoxidation reaction was carried out in the same manner as in Example 1, except that the catalytic amount was changed to 650 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 5

A vapor phase catalytic ammoxidation reaction was carried out in the same manner as in Example 1, except that the molar ratio of the starting material gas was changed to propane:ammonia:oxygen=1:1.1:2.3. The yield of acrylonitrile after 3 hours (immediately after starting) and the yield of acrylonitrile after one week, from the initiation of the vapor phase catalytic ammoxidation reaction, are set forth in Table 1.

Example 6

A vapor phase catalytic ammoxidation reaction was carried out in the same manner as in Example 1, except that the molar ratio of the starting material gas was changed to propane:ammonia:oxygen=1:1.1:3.4. The yield of acrylonitrile after 3 hours (immediately after starting) and the yield of acrylonitrile after one week, from the initiation of the vapor phase catalytic ammoxidation reaction, are set forth in Table 1.

Example 7

A vapor phase catalytic ammoxidation reaction was carried out in the same manner as in Example 1, except that the temperature of the upper space was set at 460° C. The yield of acrylonitrile after 3 hours (immediately after starting) and the yield of acrylonitrile after one week, from the initiation of the vapor phase catalytic ammoxidation reaction, are set forth in Table 1.

Example 8

A vapor phase catalytic ammoxidation reaction was carried out in the same manner as in Example 1, except that the temperature of the upper space was set at 440° C. The yield of acrylonitrile after 3 hours (immediately after starting) and the yield of acrylonitrile after one week, from the initiation of the vapor phase catalytic ammoxidation reaction, are set forth in Table 1.

Example 9

A vapor phase catalytic ammoxidation reaction was carried out in the same manner as in Example 1, except that a fluidized bed reactor 1 which was similar to that shown in FIG. 1, was in the form of a vertical cylinder having an inner diameter of 10 m and a length of 30 m, had a dispersion plate 5 at the position of 3 m from a lower end of an internal space 3 and a starting material feed opening 4 above the dispersion plate in such a way that they faced each other, and had an uppermost end of an opening of a cyclone 7 at the position of 21.0 m from an upper end of the internal space 3 was used, the catalytic amount was changed to 155000 kg, and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Example 10

A vapor phase catalytic ammoxidation reaction was carried out in the same manner as in Example 1, except that the catalyst for filling was changed to a catalyst $(Mo_1V_{0.207}Sb_{0.219}Nb_{0.102}W_{0.030}Ce_{0.005}O_n/68.0$ wt %-$SiO_2)$ described in Example 3 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 1.

Example 11

A vapor phase catalytic ammoxidation reaction was carried out in the same manner as in Example 1, except that the catalyst for filling was changed to a catalyst $(Mo_1V_{0.240}Sb_{0.250}Nb_{0.120}W_{0.030}Ce_{0.005}O_n/51.0$ wt %-$SiO_2)$ described in Example 4 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 1.

Example 12

A vapor phase catalytic ammoxidation reaction was carried out in the same manner as in Example 1, except that the catalytic amount was changed to 660 kg and the gas flow rate was changed to 530 Nm³/h as shown in Table 1. The yield of acrylonitrile after 3 hours (immediately after starting) and the yield of acrylonitrile after one week, from the initiation of the vapor phase catalytic ammoxidation reaction, are set forth in Table 1.

Comparative Example 1

A vapor phase catalytic ammoxidation reaction was carried out in the same manner as in Example 1, except that the catalytic amount was changed to 800 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Comparative Example 2

A vapor phase catalytic ammoxidation reaction was carried out in the same manner as in Example 1, except that the catalytic amount was changed to 300 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Comparative Example 3

A vapor phase catalytic ammoxidation reaction was carried out in the same manner as in Example 9, except that the catalytic amount was changed to 200000 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Comparative Example 4

A vapor phase catalytic ammoxidation reaction was carried out in the same manner as in Example 9, except that the catalytic amount was changed to 100000 kg and the gas flow rate was changed as shown in Table 1. The yield of acrylonitrile after 3 hours (immediately after starting) and the yield of acrylonitrile after one week, from the initiation of the vapor phase catalytic ammoxidation reaction, are set forth in Table 1.

Comparative Example 5

A vapor phase catalytic ammoxidation reaction was carried out in the same manner as in Comparative Example 1, except that the catalyst for filling was changed to a catalyst $(Mo_1V_{0.207}Sb_{0.219}Nb_{0.12}W_{0.030}Ce_{0.005}O_n/68.0 \text{ wt \%-SiO}_2)$ described in Example 3 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 1.

Comparative Example 6

A vapor phase catalytic ammoxidation reaction was carried out in the same manner as in Comparative Example 2, except that the catalyst for filling was changed to a catalyst $(Mo_1V_{0.207}Sb_{0.219}Nb_{0.102}W_{0.030}Ce_{0.005}O_n/68.0 \text{ wt \%-SiO}_2)$ described in Example 3 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 1.

Comparative Example 7

A vapor phase catalytic ammoxidation reaction was carried out in the same manner as in Comparative Example 1, except that the catalyst for filling was changed to a catalyst $(Mo_1V_{0.240}Sb_{0.250}Nb_{0.120}W_{0.030}Ce_{0.005}O_n/51.0 \text{ wt \%-SiO}_2)$ described in Example 4 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 1.

Comparative Example 8

A vapor phase catalytic ammoxidation reaction was carried out in the same manner as in Comparative Example 2, except that the catalyst for filling was changed to a catalyst $(Mo_1V_{0.240}Sb_{0.250}Nb_{0.120}W_{0.030}Ce_{0.005}O_n/51.0 \text{ wt \%-SiO}_2)$ described in Example 4 of Japanese Patent No. 5694379. The yield of acrylonitrile after 3 hours (immediately after starting) and the yield of acrylonitrile after one week, from the initiation of the vapor phase catalytic ammoxidation reaction, are set forth in Table 1.

TABLE 1

| | Existing amount of catalyst | | | | | | | | Discharge port | AN yield | |
| --- | --- | --- | --- | --- | --- | --- | --- | --- | --- | --- | --- |
| | Upper space ($kg/m^3$) | Lower space ($kg/m^3$) | Upper space/Lower space | Catalytic amount (kg) | Gas flow rate ($Nm^3/hr$) | Pressure in reactor (K/G) | Upper space temperature (° C.) | Superficial gas velocity (m/sec) | oxygen concentration (vol %) | Immediately after starting (%) | After one week (%) |
| Ex. 1 | 50 | 350 | 0.143 | 550 | 420 | 0.60 | 450 | 0.74 | 2 | 55.1 | 55.2 |
| Ex. 2 | 70 | 310 | 0.226 | 600 | 459 | 0.60 | 450 | 0.81 | 2 | 54.9 | 54.9 |
| Ex. 3 | 30 | 400 | 0.075 | 500 | 382 | 0.60 | 450 | 0.68 | 2 | 55 | 55 |
| Ex. 4 | 90 | 250 | 0.360 | 650 | 497 | 0.60 | 450 | 0.88 | 2 | 55.1 | 55.1 |
| Ex. 5 | 50 | 350 | 0.143 | 550 | 420 | 0.60 | 450 | 0.74 | 0.5 | 55.4 | 54.6 |
| Ex. 6 | 50 | 350 | 0.143 | 550 | 420 | 0.60 | 450 | 0.74 | 5 | 54.6 | 54.3 |
| Ex. 7 | 50 | 350 | 0.143 | 550 | 420 | 0.60 | 460 | 0.75 | 2 | 54.1 | 54.2 |
| Ex. 8 | 50 | 350 | 0.143 | 550 | 420 | 0.60 | 440 | 0.73 | 2 | 55.4 | 55.5 |
| Ex. 9 | 60 | 320 | 0.188 | 155000 | 120000 | 0.60 | 450 | 0.81 | 2 | 54.5 | 54.6 |
| Ex. 10 | 65 | 315 | 0.206 | 550 | 420 | 0.60 | 450 | 0.74 | 2 | 54.7 | 54.8 |
| Ex. 11 | 65 | 315 | 0.206 | 550 | 420 | 0.60 | 450 | 0.74 | 2 | 54.6 | 54.7 |
| Ex. 12 | 105 | 245 | 0.429 | 660 | 530 | 0.60 | 450 | 0.94 | 2 | 54.3 | 54.3 |
| Comp. Ex. 1 | 105 | 200 | 0.525 | 800 | 600 | 0.60 | 450 | 1.06 | 2 | 54.0 | —* |
| Comp. Ex. 2 | 20 | 510 | 0.039 | 300 | 250 | 0.60 | 450 | 0.44 | 2 | 53.1 | 52.8 |
| Comp. Ex. 3 | 120 | 230 | 0.522 | 200000 | 120000 | 0.60 | 450 | 0.81 | 2 | 54.2 | 54.1 |
| Comp. Ex. 4 | 20 | 510 | 0.039 | 100000 | 48000 | 0.60 | 450 | 0.32 | 2 | 49.7 | 49.5 |
| Comp. Ex. 5 | 125 | 215 | 0.581 | 800 | 600 | 0.60 | 450 | 1.06 | 2 | 52.1 | —* |
| Comp. Ex. 6 | 23 | 500 | 0.046 | 300 | 250 | 0.60 | 450 | 0.44 | 2 | 49.8 | 49.9 |
| Comp. Ex. 7 | 105 | 200 | 0.525 | 800 | 600 | 0.60 | 450 | 1.06 | 2 | 53.5 | —* |
| Comp. Ex. 8 | 20 | 510 | 0.039 | 300 | 250 | 0.60 | 450 | 0.44 | 2 | 49.7 | 49.8 |

*Continuing of reaction is impossible because of scattering of catalyst.

The present application is based on Japanese patent application (Japanese Patent Application No. 2017-130390) filed with Japan Patent Office on Jul. 3, 2017, and the contents thereof are incorporated herein by reference.

INDUSTRIAL APPLICABILITY

The present invention has industrial applicability as a process for producing unsaturated nitrile.

REFERENCE SIGNS LIST

1: fluidized bed reactor, 2: catalyst, 3: internal space, 3a: upper space, 3b: lower space, 4: starting material feed opening, 5: dispersion plate, 6: discharge port, 7: cyclone, 7A-C: multi-stage cyclone, 7a: inlet, 8: dispersion tube, 9: feed opening, A: starting material gas, B: oxygen-containing gas, C: reaction product gas

The invention claimed is:

1. A process for producing unsaturated nitrile, the process comprising:
providing a fluidized bed reactor having an internal space comprising a catalyst capable of being fluidized therein, a starting material feed opening to feed a starting material gas comprising hydrocarbon to the internal space, a dispersion plate to feed an oxygen-containing gas comprising oxygen to the internal space; a discharge port to discharge a reaction product gas from the internal space, and a cyclone to separate and recover the catalyst from the reaction product gas in the internal space; and
a reaction step of subjecting the hydrocarbon to a vapor phase catalytic ammoxidation reaction in the presence of the catalyst in the internal space to produce the corresponding unsaturated nitrile, wherein
when the internal space is divided into two spaces of an upper space occupying a space from an upper end of an inlet of the cyclone to an upper end of the internal space and a lower space occupying a space below the upper end of the inlet of the cyclone and ranging to the dispersion plate, a ratio of an existing amount of the catalyst in the upper space per unit volume to an existing amount of the catalyst in the lower space per unit volume is 0.05 to 0.45 in the reaction step, and
the catalyst has a composition represented by the following formula (1):

$$Mo V_a Nb_b X_c T_d Z_e O_n \qquad (1)$$

wherein X is one or more element selected from the group consisting of Sb and Te, T is one or more element selected from the group consisting of W and Mn, and Z is Ce, and
a, b, c, d, e and n each represents an atomic ratio of each atom per Mo atom, and are in the ranges of $0.01 \leq a \leq 1$, $0.01 \leq b \leq 1$, $0.01 \leq c \leq 1$, $0 \leq d \leq 1$, and $0 \leq e \leq 1$, and n is a value satisfying a balance of the valences.

2. The process for producing unsaturated nitrile according to claim 1, wherein the existing amount of the catalyst in the upper space per unit volume is 10 kg/m$^3$ or more and 100 kg/m$^3$ or less in the reaction step.

3. The process for producing unsaturated nitrile according to claim 1, wherein the existing amount of the catalyst in the lower space per unit volume is 150 kg/m$^3$ or more and 600 kg/m$^3$ or less in the reaction step.

4. The process for producing unsaturated nitrile according to claim 1, wherein a superficial gas velocity in the upper space is less than 1.0 m/sec in the reaction step.

5. The process for producing unsaturated nitrile according to claim 1, wherein an oxygen concentration in the reaction product gas discharged from the discharge port is 0.5 to 5.0 vol % in the reaction step.

6. The process for producing unsaturated nitrile according to claim 1, wherein the hydrocarbon is propane and/or propylene.

* * * * *